United States Patent [19]
Kwok et al.

[11] Patent Number: 5,886,200
[45] Date of Patent: Mar. 23, 1999

[54] PROCESS FOR THE PREPARATION OF 17-ESTERS OF 9 α, 21-DIHALO-PREGNANE-11 β, 17 α-DIOL-20-ONES

[75] Inventors: Daw-Iong Albert Kwok, Gillette; David J. S. Tsai, Warren; Chou-Hong Tann, Berkeley Heights; Xiaoyong Fu, Edison, all of N.J.

[73] Assignee: Schering Corporation, Kenilworth, N.J.

[21] Appl. No.: 881,811

[22] Filed: Jun. 25, 1997

Related U.S. Application Data

[60] Provisional application No. 60/021,167 Jul. 1, 1996.
[51] Int. Cl.[6] ........................................ C07J 5/00
[52] U.S. Cl. ..................... 552/577; 552/574; 552/576
[58] Field of Search ................... 552/574, 576, 552/577

[56] References Cited

U.S. PATENT DOCUMENTS

| | | | |
|---|---|---|---|
| 2,713,587 | 7/1955 | Bergstrom | 260/397.45 |
| 2,793,207 | 5/1957 | Ralls et al. | 260/239.5 |
| 3,440,252 | 4/1969 | Weir | 260/397.45 |
| 3,502,700 | 3/1970 | Krakower et al. | 260/397.45 |
| 4,472,393 | 9/1984 | Shapiro | 424/243 |

FOREIGN PATENT DOCUMENTS

WO92/04365  9/1990  WIPO .

OTHER PUBLICATIONS

Hesk et al., Synthesis of Tritium Labelled Mometasone Furoate, J. Labelled Compds Radiopharm., vol. 33(5), pp. 439–442, 1993.
Popper et al., J. steroid Biochem., 1987, 27 No. 4–6, pp. 837–843: "Structure–Activity Relationships of a Series of Novel Topical Corticosteroids".
Puar et al., Steroids, 1995, 60, pp. 612–614: An unusual rearrangement product formed during production of mometasone furoate (Sch 32088).
Shapiro et al., J. Med. Chem., 1987, 30, pp. 1581–1588: "17–Heteroaroyl Esters of Cortico–steroids. 2. 11β–Hydroxy Series".
Abstract of Netherlands Patent Application 8400910.

*Primary Examiner*—JoséG. Dees
*Assistant Examiner*—Alton Pryor
*Attorney, Agent, or Firm*—Arthur Mann; Anita W. Magatti

[57] ABSTRACT

The invention provides an improved process for the preparation of 17-esters of 9α,21-dihalo-pregnane-11β,17α-diol-20-ones, and in particular for the preparation of 17-esters of anti-inflammatory steroids according to the following scheme:

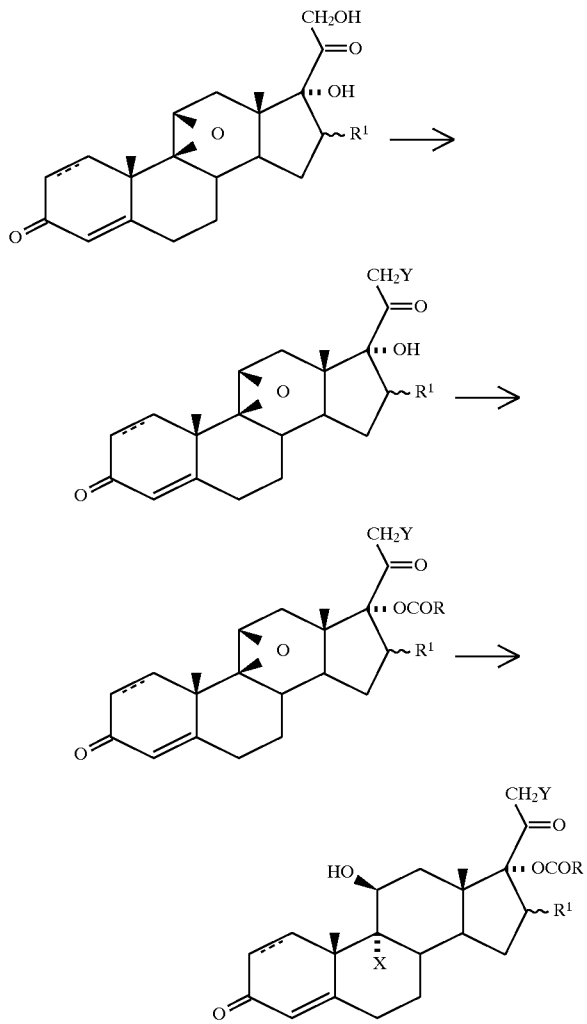

wherein RCO, $R^1$, X, Y and the dotted line are as defined in the specification. The novel process is especially suitable for the preparation of Mometasone Furoate.

23 Claims, No Drawings

PROCESS FOR THE PREPARATION OF 17-ESTERS OF 9 α, 21-DIHALO-PREGNANE-11 β, 17 α-DIOL-20-ONES

This application claims the benefit of U.S. Provisional Application No. 60/021,167, filed on Jul. 1, 1996.

FIELD OF THE INVENTION

This invention relates to a new process for the synthesis of 17-esters of 9α,21-dihalo-pregnane-11β,17α-diol-20-ones, in particular to the synthesis of Mometasone Furoate, a synthetic anti-inflammatory steroid useful in the treatment of inflammatory disease.

BACKGROUND OF THE INVENTION

Mometasone Furoate, otherwise known as 9α,21-dichloro-11β,17α-dihydroxy-16α-methyl-1,4-pregnadien-3,20-dione 17-(2'-furoate), is a potent anti-inflammatory steroid having the structure:

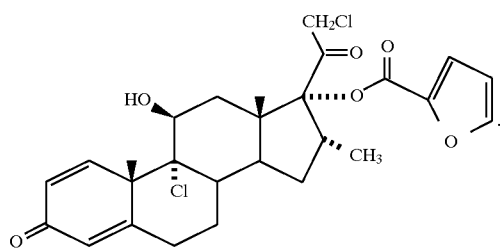

It is described in U.S. Pat. No. 4,472,393, specifically in Example 12. Example 12 describes two processes for the preparation of Mometasone Furoate, Methods I and II, which use as starting materials 9β,11β-epoxy-17α,21-dihydroxy-16α-methyl-1,4-pregnadien-3,20-dione and 21-chloro-17α-hydroxy-16α-methyl-1,4,9(11)-pregnatrien-3,20-dione, respectively. Only Method I therein is relevant to the present invention; it can be illustrated as follows:

METHOD I in Example 12 of U.S. Pat. No. 4,472,393:

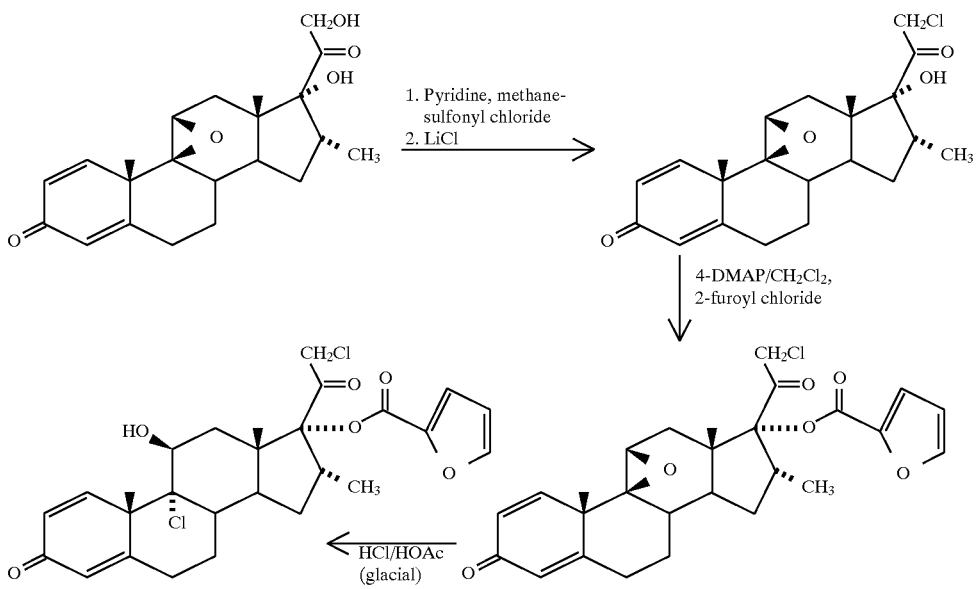

(where 4-DMAP is 4-dimethylaminopyridine). The process of Example 12, Method I, is carried out in three separate and distinct stages, as indicated in the above scheme.

Further study of this process has indicated that a number of steroidal by-products are formed at each stage, so that yields are reduced and elaborate purification is required. Thus, the first stage (introduction of the 21-chlorine atom) yields also a hydroxysultone (see below), a 9α,11β-chlorohydrin, and a 21-pyridinium salt (this last compound amounting to some 5% of the product by NMR analysis). The second stage, esterification to introduce the 17-(2-furoyl-oxy) group, typically produces about 4–6% yield of the enol difuroate epoxide (a 21-chloro-9α,11β-epoxy-20(21)-en-17α,20-diol 17,20-difuroate). We have determined that the sultone and the enol difuroate epoxide have the following structures:

sultone: 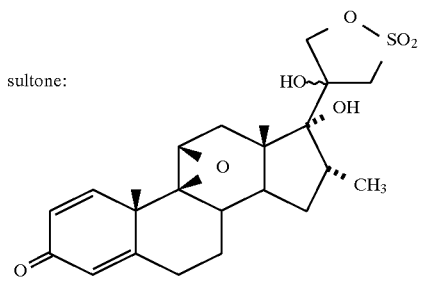

3
-continued enol difuroate epoxide:

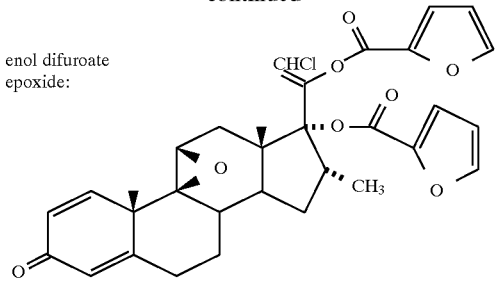

The third stage (opening the epoxide ring) typically yields about 7–8% of two degradation products having an aromatized Ring A with the 9,10-bond broken. All these steps, therefore, introduce impurities, so that the yield of desired product is thereby reduced, and the final product needs careful purification, resulting in further losses.

It is therefore an object of the present invention to provide an improved process for the preparation of Mometasone Furoate and related 17-esters of 9α,21-dihalo-pregnane-11β,17α-diol-20-ones, especially anti-inflammatory steroids.

SUMMARY OF THE INVENTION

The present invention provides a process for the preparation of a 17-ester of a 9α,21-dihalo-pregnane-11β,17α-diol-20-one, which comprises:

(1). reacting a 9β,11β-epoxy-pregnane-17α,21-diol-20-one with an excess of an organic (aromatic or alkyl) sulfonyl halide, in the presence of a trialkylamine and an inert organic solvent to form the 21-sulfonate ester, and then adding to the reaction mixture an alcohol in an amount substantially equivalent to the excess of sulfonyl halide, to yield a 9β,11β-epoxy-21-halo-pregnane-17α-ol-20-one;

(2). reacting the resulting 9β,11β-epoxy-21-halo-pregnane-17α-ol-20-one with an anhydride, chloride, or bromide of a carboxylic acid in the presence of a trialkylamine, to form the 17-ester of the 9β,11β-epoxy-21-halo-pregnane-17α-ol-20-one; and then (3). reacting the resulting 9β,11β-epoxy-21-halo-pregnane-17α-ol-20-one 17-ester with aqueous hydrogen halide in the presence of an inert organic solvent to form the 17-ester of the 9α,21-dihalo-pregnaney-11β,17α-diol-20-one.

The present invention also provides a process for the preparation of a steroid of the formula II:

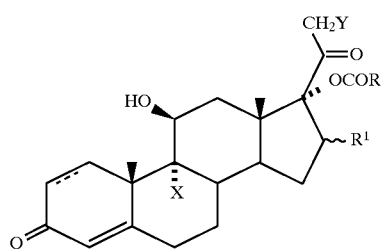

wherein:
X is a fluorine, chlorine or bromine atom;
Y is a fluorine, chlorine or bromine atom;
RCO (or COR) is a carboxylic acyl group;
$R^1$ is hydrogen or a lower alkyl group (in the α- or β-configuration);
and the broken line at the 1,2-positions indicates a single bond or a double bond;
which comprises:

4

A. reacting a compound of the formula III:

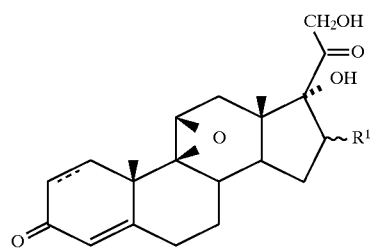

wherein $R^1$ and the dotted line are as defined above;

with about 0.03 to about 3 mol equivalents excess of an organic (aromatic or alkyl) sulfonyl fluoride, chloride or bromide in the presence of a trialkylamine and an inert organic solvent to form the 21-sulfonate ester, and then adding to the reaction mixture a lower primary alkanol in an amount substantially equivalent to the excess of sulfonyl halide, to yield a compound of the formula IV:

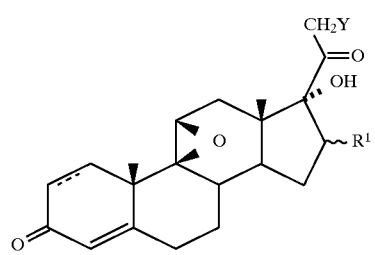

wherein $R^1$, Y and the dotted line are as defined above;

B. reacting the resulting compound of the formula IV with an anhydride, chloride, or bromide of a carboxylic acid RCOOH, wherein RCO is as defined above, in the presence of a trialkylamine, to form a compound of the formula V:

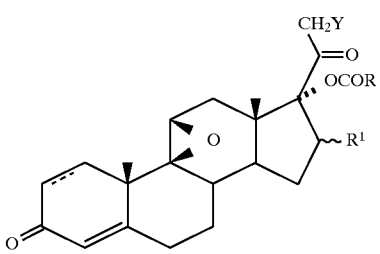

wherein RCO, $R^1$, Y and the dotted line are as defined above; and then

C. reacting the resulting compound of the formula V with aqueous HX, wherein X is as defined above, in the presence of an inert water-immiscible organic solvent to form a compound of the formula II defined above.

The present invention also provides a process for the preparation of a steroid of the formula IIA:

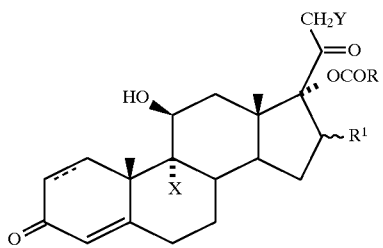

wherein:

X is a fluorine, chlorine or bromine atom;

Y is an iodine atom;

RCO is a carboxylic acyl group;

R$^1$ is hydrogen or an alkyl group (in the α- or β-configuration);

and the broken line at the 1,2-positions indicates a single bond or a double bond;

which comprises:

A. reacting a compound of the formula IIIA:

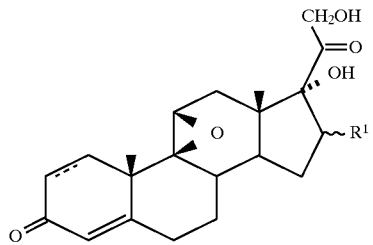

wherein R$^1$ and the dotted line are as defined above;

with about 0.03 to about 3 mol equivalents excess of an organic (aromatic or alkyl) sulfonyl chloride or bromide in the presence of a trialkylamine and an inert organic solvent to form the 21-sulfonate ester, and then adding to the reaction mixture an alkanol substantially equivalent to the excess of sulfonyl halide and at least one equivalent of an ionic iodide, to yield a compound of the formula IVA:

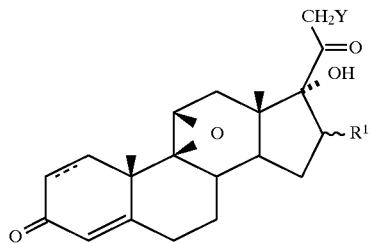

wherein R$^1$, Y and the dotted line are as defined above;

B. reacting the resulting compound of the formula IVA with an anhydride, chloride, or bromide of a carboxylic acid RCOOH, wherein RCO is as defined above, in the presence of a trialkylamine, to form a compound of the formula VA:

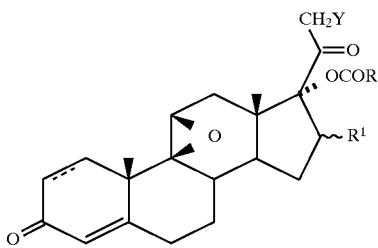

wherein RCO, R$^1$, Y and the dotted line are as defined above; and then

C. reacting the resulting compound of the formula VA with aqueous HX, wherein X is as defined above, in the presence of an inert organic solvent to form a compound of the formula II defined above.

DETAILED DESCRIPTION OF THE PREFERRED EMBODIMENTS

In the present process for the preparation of a 17-ester of a 9α,21-dihalo-pregnane-11β,17α-diol-20-one:

step (1) (reaction of a 9β,11β-epoxy-pregnane-17α,21-diol-20-one with an organic (aromatic or alkyl) sulfonyl halide) is preferably carried out with about 0.01 to about 3 mol equivalents excess of the sulfonyl halide, which is preferably an aromatic sulfonyl fluoride or especially the chloride or bromide; the amine is preferably a tri(lower alkyl)amine; the inert organic solvent is preferably water-immiscible; and the alkanol is preferably a lower primary alkanol, e.g., methanol;

step (2) (reaction of the resulting 9β,11β-epoxy-21-halo-pregnane-17α-ol-20-one with an anhydride, chloride, or bromide of a carboxylic acid) is preferably carried out with the chloride of a heteroaryl carboxylic acid, in the presence of a tri(lower alkyl)amine; and step (3) (reaction of the resulting 9β,11β-epoxy-21-halo-pregnane-17α-ol-20-one 17-ester with aqueous hydrogen halide in the presence of an inert organic solvent) is preferably carried out with aqueous HF, aqueous HCl, or aqueous HBr, more especially with aqueous HCl in the presence of an inert organic solvent which is water-immiscible, and in the presence of a water-miscible organic co-solvent.

Similar conditions apply to steps A, B and C respectively of the process for the preparation of a steroid of the formula II or IIA defined above.

The present invention provides a novel process for the preparation of 17-esters of 9α,21-dihalo-11β,17α-dihydroxy-20-keto steroids and especially for the preparation of anti-inflammatory 17-esters of 9,21-dihalo-11β,17α-dihydroxy steroids of the pregnane series. Moreover, the novel process has a number of advantages over known methods, more specifically over the process outlined under Method I in Example 12 of U.S. Pat. No. 4,472,393 for the preparation of Mometasone Furoate and for analogous anti-inflammatory steroids. Thus, the amount of wasted by-products produced in the present process can be considerably reduced relative to the process of Method I above, and the novel process can be carried out as an in situ (or one-pot) reaction in a single organic solvent instead of three separate and distinct steps using three different solvents, in less time, and with the use of smaller volumes of solvent. More specifically, the preparation of Mometasone Furoate can proceed with up to 50% higher yield than that of Method I in U.S. Pat. No. 4,472,393, and in only half the time. Moreover, several reagents necessary in the process of Method I can be dispensed with, and the amount of methylene chloride used, a potential carcinogen, can be reduced by half.

In the present specification, terms have the following meanings unless otherwise specified:

"Alkyl" represents a saturated aliphatic group having 1 to 12 carbon atoms, and "lower alkyl" represents a saturated aliphatic group having 1 to 4 carbon atoms, especially a methyl or ethyl group;

"Aromatic" in relation to 'aromatic sulfonyl halide' represents a benzene or naphthalene nucleus having 0, 1 or 2 substituents selected from halogen atoms and lower alkyl groups, with the bond to the sulfonyl group extending from the nucleus;

"Halogen" represents fluorine, chlorine, bromine or iodine;

An "acyl" group of a carboxylic acid RCOOH is the group RCO (actually shown as 'COR' in chemical formulae herein), and can be exemplified by alkyl—C(O)—, alkenyl—C(O)—, cycloalkyl—C(O)—, aryl—C(O)—, or heteroaryl—C(O)—;

"Alkenyl" represents a straight or branched aliphatic hydrocarbon group having at least one carbon-to-carbon double bond and having from 2 to 10 carbon atoms, preferably from 2 to 6;

"Aryl" represents a carbocyclic group having from 6 to 10 carbon atoms and having at least one benzenoid ring, with all available substitutable carbon atoms of the carbocyclic group being intended as possible points of attachment, said carbocyclic group being optionally substituted with 1 to 3 Q groups, where each group Q is independently selected from halo, alkyl, hydroxy, alkoxy, phenoxy, and dialkylamino groups. Preferred aryl groups are phenyl, substituted phenyl, 1-naphthyl, 2-naphthyl and indanyl;

"Cycloalkyl" represents a saturated carbocyclic group having from 3 to 10 carbon atoms, preferably from 3 to 6;

"Heteroaryl" represents a cyclic aromatic group having at least one O, S and/or N (e.g., 1–4, preferably 1–3, especially 1 or 2) interrupting a carbocyclic ring structure and having a sufficient number of delocalized electrons to provide aromatic character, with the aromatic heterocyclic group having from 2 to 9, preferably 4 or 5 carbon atoms, e.g., 2-, 3- or 4-pyridyl, 2- or 3-furyl, 2- or 3-thienyl, 2-, 4- or 5-thiazolyl, 2-, 4- or 5-imidazolyl, 2-, 4- or 5-pyrimidinyl, 2-pyrazinyl, 3- or 4-pyridazinyl, 3-, 5- or 6-[1,2,4-triazinyl], 3- or 5-[1,2,4-thiadiazolyl], 2-, 3-, 4-, 5-, 6- or 7-benzofuranyl, 2-, 3-, 4-, 5-, 6- or 7-indolyl, 3-,4- or 5-pyrazolyl, or 2-, 4- or 5-oxazolyl, etc. Preferred heteroaryl groups include 2-, 3- or 4-pyridyl, 2- or 3-furyl, 2- or 3-thienyl, 2-, 4- or 5-imidazolyl or 7-indolyl;

"Heteroaroyl" represents heteroaryl-C(O)—, wherein heteroaryl is as defined above and is preferably 2-, 3- or 4-pyridyl, 3- or especially 2-furyl, 2- or 3-thienyl, 2-, 4-, or 5-imidazolyl or 7-indolyl.

In the compounds of formula II or IIA:

X is preferably fluorine or chlorine;

$R^1$ is preferably in the α-configuration and is especially a methyl group;

the broken line at the 1,2-positions preferably indicates a double bond;

and the group RCO is preferably a heterocyclic-carbonyl group. The heterocycle (R in these preferred compounds) is preferably a 5-membered heterocycle containing an O or S atom. The heterocyclic-carbonyl is for example 2- or 3-furoyl, or 2- or 3-thenoyl, especially 2-furoyl.

In the compounds of formula II, Y is preferably bromine or most preferably chlorine.

Compounds that can be prepared by the present process include:

The 17-(2-thenoate), 17-(3-thenoate), 17-(2-furoate) esters, and especially the 17-(3-furoate) ester, of 9α,21-dichloro-11β,17α-dihydroxy-16α-methyl-1,4-pregnadien-3,20-dione;

the 17-(2-thenoate), 17-(3-thenoate), 17-(2-furoate), and 17-(3-furoate) esters of 9α-fluoro-21-chloro-11β,17α-dihydroxy-16α-methyl-1,4-pregnadien-3,20-dione;

the 17-(2-thenoate), 17-(3-thenoate), 17-(2-furoate), and 17-(3-furoate) esters of 9α-bromo-21-chloro-11β,17α-dihydroxy-16α-methyl-1,4-pregnadien-3,20-dione;

and their 6α-fluoro derivatives.

In the following paragraphs: 'the first step' refers to Step (1) or Step A above; 'the second step' refers to Step (2) or Step B above; and 'the third step' refers to Step (3) or Step C above.

In the first step, the sulfonyl halide is preferably an aromatic sulfonyl halide, so that formation of a sultone (a frequent byproduct if the sulfonyl halide is an alkyl sulfonyl halide) can be avoided. The sulfonyl halide is preferably a sulfonyl chloride or bromide, especially a chloride, and its aromatic group may be a benzene or naphthalene nucleus. In particular, the aromatic group is preferably a benzene nucleus which may be substituted with a chlorine atom or a methyl group, preferably in the 4-position. Thus the aromatic sulfonyl halide may be benzenesulfonyl chloride, 4-chlorobenzenesulfonyl chloride, or especially 4-toluenesulfonyl chloride. Other sulfonyl halides that can be used include methane- and ethane-sulfonyl chloride and bromide.

The trialkylamine functions as base and acid-binding agent. Any trialkylamine that is able to fulfill those functions and is readily removable from the reaction mixture with aqueous acid is suitable. Thus trialkylamines usable in the process of the present invention include tri(lower alkyl) amines such as dimethylethylamine, triethylamine, tripropylamine, tri(2-propyl)amine, N,N-di(2-propyl) ethylamine and tributylamine. Triethylamine is effective and is especially preferred on account of its availability and low cost. The aromatic sulfonyl halide reacts to form the 21-sulfonate ester, and its halide is bound, e.g. as tri(lower alkyl)amine hydrochloride or hydrobromide.

The inert organic solvent is preferably a non-polar water-immiscible solvent, and is conveniently methylene chloride, $CH_2Cl_2$. Other usable solvents include carbon tetrachloride, cyclohexane, and aromatic hydrocarbons such as benzene and toluene.

The sulfonyl halide is preferably used in a small excess, e.g., in about 1.1 to 2.5 equivalents altogether, more preferably about 1.3 to 2 equivalents, e.g., 1.5 to 1.8 equivalents (i.e., about 0.5 to 0.8 equivalent excess). The trialkylamine (preferably tri(lower alkyl)amine) is used in a small to moderate excess, e.g., in about 2 to 6 equivalents altogether, preferably about 3 to 4 equivalents.

The reaction is preferably carried out at moderate to low temperature, e.g., at −20° C. to room temperature, more preferably at about −10° to 10° C., for 1–10 hours. The reaction is allowed to go to completion, i.e., until essentially all of the steroid of the formula HI or HIA has been converted into its 21-sulfonate ester. The reaction typically takes a few hours, e.g., about 3–4 hours at −5° to +5° C. for conversion of 9β,11β-epoxy-17α,21-dihydroxy-16α-methyl-1,4-pregnadien-3,20-dione into its 21-tosylate.

Then a small amount of an alcohol (e.g., a lower primary alkanol such as methanol) is added to the reaction mixture, substantially equivalent to the excess of sulfonyl halide, with which it forms a sulfonate ester, e.g., a lower alkyl aromatic-sulfonate ester, although a very small excess of alkanol is preferred, e.g., 0.01 to 0.2, preferably 0.05 to 0.1 equivalent excess. The addition of alcohol quenches the excess of sulfonyl halide and releases further halide ion which is capable of displacing the 21-sulfonate ester group. The addition of methanol strongly reduces the amount of impurities otherwise formed and increases the rate of displacement of the 21-sulfonate ester by halide (fluoride, chloride or bromide). There is no need in this improved process to add a further halide to effect replacement of the 21-sulfonate ester by fluoride, chloride or bromide; halide already present in the reaction mixture effects the necessary displacement. Thus, addition of a chloride or bromide such as LiCl or LiBr (as in the process of Method I of Example 12 of U.S. Pat. No. 4,472,393) is unnecessary. However, to produce a 21-iodide, a soluble iodide such as potassium iodide or a tetraalkylammonium iodide should be added to the reaction mixture.

This reaction is conveniently carried out for a few hours at a moderate temperature, e.g., at 20°–50° C., preferably at 30°–40° C. When methylene chloride is present as solvent, the reaction can be carried out just below reflux temperature (i.e., a little below 40° C.) for 4–8, preferably 5–6 hours. For example, conversion of 9β,11β-epoxy-17α,21-dihydroxy-16α-methyl-1,4-pregnadien-3,20-dione 21-tosylate into 21-chloro-9β,11β-epoxy-17α-hydroxy-16α-methyl-1,4-pregnadien-3,20-dione typically takes a few hours, e.g., about 4–8 hours a little below reflux temperature in methylene chloride.

The esterification of the second step, to introduce the esterifying group RCO which is as defined above, is then carried out, preferably by the addition of an acyl bromide RCOBr or especially the chloride RCOCl, although an anhydride RCOOCOR or a mixed anhydride RCOOR$^2$, wherein R$^2$ is an acyl group of a strongly hindered acid such as trimethylacetic acid, can also be used. The preferred ester-forming derivative is the acid chloride, e.g., 2-furoyl chloride. The esterification is carried out in the presence of a trialkylamine as base; so that the reaction can be performed without isolation or purification of the product from the first (previous) step, the same tri(lower alkyl)amine, e.g., triethylamine, is preferably used as base in this second step. An excess of the ester-forming derivative is preferably used, e.g., from 1.2 to 2.5 mole altogether, preferably from 1.5 to 2.0 mole altogether, in particular about 1.8 mole. The reaction is effected at moderate to low temperature, typically 0°–30° C. and especially at or below room temperature, for several hours, e.g., 5°–15° C. for 5–15 hours. When 21-chloro-9β,11β-epoxy-17α-hydroxy-16α-methyl-1,4-pregnadien-3,20-dione is converted into 21-chloro-9β,11β-epoxy-17α-hydroxy-16α-methyl-1,4-pregnadien-3,20-dione 17-(2'-furoate) by reaction with 2-furoyl chloride in triethylamine and methylene chloride (retained as solvent from the first step), the reaction is typically complete in 10–14 hours, e.g., about 12 hours, at 5°–15° C., e.g., about 12 hours at about 10° C.

The base (tri(lower alkyl) amine) is next removed by washing the reaction solution resulting from the second step with aqueous acid. A dilute strong mineral acid such as sulfuric acid is convenient. Hydrochloric or hydrobromic acid can also conveniently be used when that acid will be used in the third step for the production of a 9α-chloro- or 9α-bromo-steroid, respectively, by opening the epoxide ring.

The final or third step, opening the 9β,11β-epoxide ring to form the 9α-halo-11β-hydroxy steroid of formula II or IIA, is then effected by means of the required hydrogen halide in aqueous solution. Concentrated aqueous hydrogen halide (wherein the halide is fluoride, chloride or bromide) is added to the solution of the steroid of the formula IV or IVA, together with an inert water-miscible organic solvent such as a lower alkanoic acid having 2 to 4 carbon atoms, especially glacial acetic acid, a lower ketone such as acetone, a lower alkanol such as ethanol, DMF, DMSO, THF, dioxan, 1,2-dimethoxyethane. The inert water-immiscible organic solvent from the first and second steps, typically methylene chloride, is carried through this third step also. This reaction is preferably carried out with a large excess (e.g., 10–20 equivalents, preferably about 15 equivalents) of the hydrogen halide, since the reaction is essentially two-phase; it therefore requires agitation, e.g., by stirring. It typically takes a few hours at low to moderate temperature, e.g., 1–4 hours at 0°–20° C. When 21-chloro-9β,11β-epoxy-17α-hydroxy-16α-methyl-1,4-pregnadien-3,20-dione 17-(2'-furoate) is converted into 9α,21-dichloro-11β,17α-dihydroxy-16α-methyl-1,4-pregnadien-3,20-dione 17-(2'-furoate) by reaction with 12N aqueous HCl, about 15 equivalents, in the presence of acetic acid and methylene chloride, the reaction is preferably carried out at about 0° C. for 1–3 hours and then at about 20° C. for about 1–3 hours.

The steroid product can then be isolated by standard procedures such as 30 washing to remove water-soluble materials, especially acids, and then isolation and recrystallization. In the isolation of 9α,21-dichloro-11β,17α-dihydroxy-16α-methyl-1,4-pregnadien-3,20-dione 17-(2'-furoate) it is especially advantageous to replace the methylene chloride with methanol by distillation; the steroid precipitates and can be filtered off and recrystallized from $CH_2Cl_2$ and $CH_3OH$ to yield Mometasone Furoate of pharmaceutical purity.

In particular, the present invention provides an improved process for the preparation of 9α,21-dichloro-11β,17α-dihydroxy-16α-methyl-1,4-pregnadien-3,20-dione 17-(2'-furoate), which comprises:

A1. reacting 9β,11β-epoxy-17α,21-dihydroxy-16α-methyl-1,4-pregnadien-3,20-dione with 4-toluenesulfonyl chloride in the presence of triethylamine and methylene chloride to form the 21-tosylate, and then adding methanol whereby 21-chloro-9β,11β-epoxy-17α-hydroxy-16α-methyl-1,4-pregnadien-3,20-dione is formed;

B1. reacting 21-chloro-9β,11β-epoxy-17α-hydroxy-16α-methyl-1,4-pregnadien-3,20-dione (without isolation) with 2-furoyl chloride in the presence of triethylamine to yield 21-chloro-9β,11β-epoxy-17α-hydroxy-16α-methyl-1,4-pregnadien-3,20-dione 17-(2'-furoate), and then removing triethylamine and other water-soluble materials with an acid wash (preferably with a mineral acid such as aqueous HCl); and C1. reacting 21-chloro-9β,11β-epoxy-17α-hydroxy-16α-methyl-1,4-pregnadien-3,20-dione 17-(2'-furoate) (without isolation) with concentrated aqueous HCl in the presence of acetic acid to yield 9α,21-dichloro-11β,17α-dihydroxy-16α-methyl-1,4-pregnadien-3,20-dione 17-(2'-furoate).

Step A1 is preferably carried out with a small excess (about 0.4 to 1.0 equivalents excess) of 4-toluenesulfonylchloride in about 3–5 equivalents of triethylamine and sufficient methylene chloride (e.g., about 6 volumes, where 'one volume' indicates one liter for each kilogram of steroid) at reduced temperature, e.g. at −5° to 5° C. for 2–4 hours. Then sufficient methanol, preferably in 0.01 to 0.1 equivalent excess in relation to the sulfonylchloride, is added to quench the excess of 4-toluenesulfonylchloride, and the reaction mixture is heated near (a little below) reflux, e.g., 35°–40° C., for 4–8 hours. During this period the chloride liberated from the 4-toluenesulfonylchloride displaces the 21-(4-toluenesulfonyloxy) group, and the 21-chloro compound, 21-chloro-9β,11β-epoxy-17α-hydroxy-16α-methyl-1,4-pregnadien-3,20-dione, is produced, substantially without the formation of impurities characteristic of Method I of U.S. Pat. No. 4,472,393, Example 12.

There is no need to isolate this compound to perform Step B1; the reaction mixture is cooled to about −5° to 0° C., and a small excess (e.g., 1.5 to 2 equivalents altogether) of 2-furoylchloride is added. The triethylamine, base in Step A1, functions again as base, although it is usually desirable to add a further quantity, e.g., 1–5 equivalents, preferably 3–4 equivalents. The 17-ester, 21-chloro-9β,11β-epoxy-17α-hydroxy-16α-methyl-1,4-pregnadien-3,20-dione 17-(2'-furoate), is formed. The esterification is preferably carried out at reduced temperature, e.g., 5°–15° C., for about 10–14 hours.

Again there is no need to isolate the product (the 17-ester); at the end of Step B1, the reaction mixture is simply washed with dilute mineral acid, preferably aqueous HCl, to remove triethylamine (and other water-soluble materials). Then, in Step C1, the washed reaction mixture is cooled to about 0° C., a large excess (e.g., 10–15 equivalents) of concentrated (12N) HCl is added, together with 0.5 to 2 volumes of glacial acetic acid. This reaction is preferably carried out with stirring at 0° C. for a short time, e.g., about 1–3 hours, and then at room temperature (about 20° C.) for about 1–3 hours.

This process can be presented as follows:

In this scheme, TsCl is 4-toluenesulfonylchloride, TEA is triethylamine, and 2-Fu—Cl is 2-furoylchloride.

The process of this scheme has several advantages over that of Method I (U.S. Pat. No. 4,472,393) shown in the Background section. The use of 4-toluene-sulfonylchloride in Step A1 eliminates the formation of the hydroxy-sultone (since there is no activated methyl or methylene group on the sulfur atom of the 4-toluenesulfonylchloride). Furthermore, the use of triethylamine as base (in a small excess) largely eliminates the formation of the 21-quaternary ammonium salt; triethylamine has a much smaller tendency than pyridine (used in large excess as solvent) and 4-dimethylaminopyridine to form such a salt. Moreover, the amount of 9α-chloro-11β-hydroxy product (formed by premature opening of the 9β,11β-epoxide ring) is strongly reduced. Furthermore, the use of lithium chloride to displace the 21-sulfonate ester group is eliminated. In addition, the solution yield of the 21-chloro compound is raised from about 77% to about 98%. The reaction mixture can be put through the next step as it is; no work-up or purification should be necessary.

In Step B1, the use of triethylamine as base instead of 4-DMAP strongly reduces the formation of the above-mentioned enol difuroate byproduct of the corresponding step in Method I (the 21-chloro-20(21)-en-17α,20-diol 17,21-difuroate): from about 4–6% in the process of Method I to less than 1% (e.g., about 0.5%) in Step B1. Furthermore, the solution yield of the 17-(2'-furoate) ester is raised from about 82% to about 97%. After the washing with mineral acid, the reaction mixture can be carried through the next step as it is; no workup or purification should be necessary.

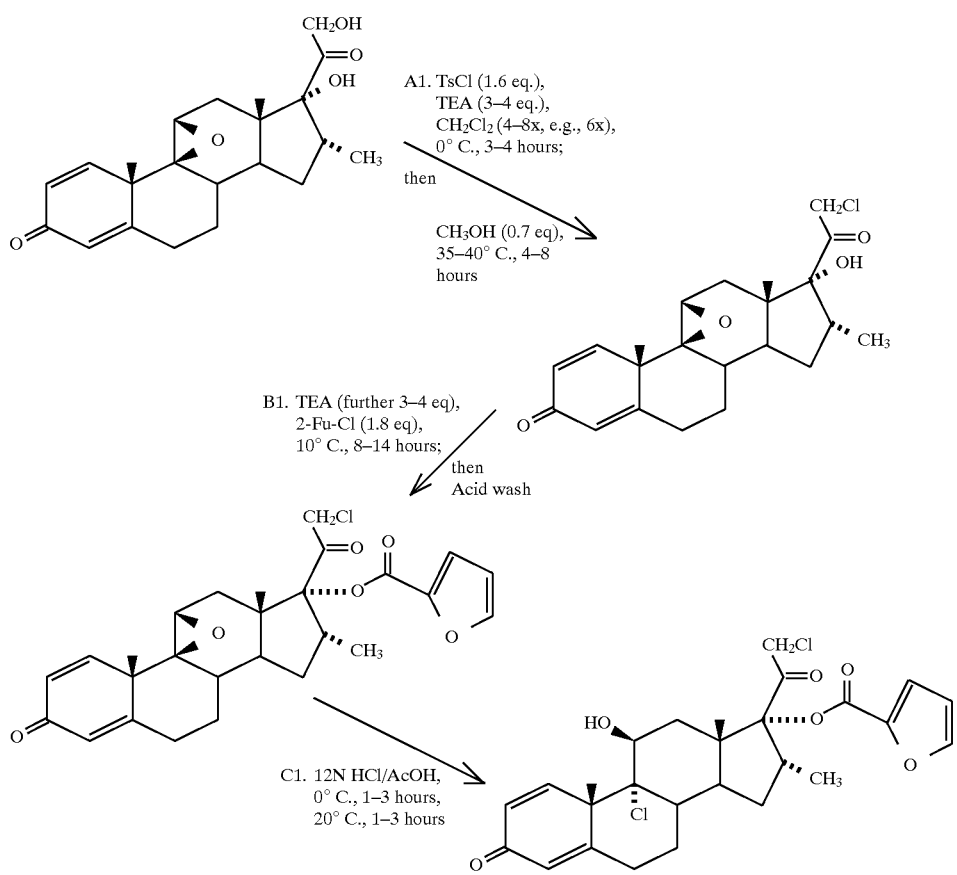

In Step C1, the use of a two-phase system together with careful control of the temperatures—starting the reaction at about 0° C. and completing it at about 20° C.—reduces the yield of the byproducts that have an aromatized ring A with the 9–10 bond broken from about 7–8% to less than 3%. Furthermore, the solution yield of the 9α,21-dichloro-11β-hydroxy compound is raised from about 83% to about 95%. HPLC shows that about 95% conversion to the desired product has taken place.

Moreover, the general reduction in byproducts in Step A1 relative to the corresponding step of Method I means that much less byproduct is produced and is carried through Steps B1 and C1; similarly, the reduction in byproducts in Step B1 relative to the corresponding step of Method I means that much less byproduct is produced there and is carried through Step C1. Consequently, the present process provides a significantly greater yield of purer product than does Method I of U.S. Pat. No. 4,472,393; and this purer product can be purified by simple methods such as solvent replacement and recrystallization instead of column chromatography. All these are very significant advantages, especially when the process is run on a commercial scale.

Another advantage of the present process is that it can be carried out as a 'one-pot' process, without isolation and purification of intermediates. This is primarily because of the new invention of the new and efficient reaction Steps A1, B1 and C1, which were carefully designed and developed to be run in the same solvent, most preferably $CH_2Cl_2$. This invention thus provides a process for the preparation of Mometasone Furoate of greatly enhanced efficiency. As a consequence, the total time needed to put a batch through the process can be reduced from 8 days to 4. Moreover, the overall yield of the process is increased from about 52% to about 80%, based on the recrystallized product, and the product is of better quality. Furthermore, the novel process is environmentally friendly, in that (for example) it avoids the use of pyridine, 4-DMAP, lithium chloride, and silica gel (for chromatographic purification), and it reduces by about 50% the use of methylene chloride (a potential carcinogen). The novel process, especially in its preferred embodiments for the preparation of 9α,21-dichloro-11β,17α-dihydroxy-16α-methyl-1,4-pregnadien-3,20-dione 17-(2'-furoate) [Mometasone Furoate], thus has great commercial advantage and presents a very significant advance in the art.

EXAMPLES

The following Examples illustrate but do not in any way limit the present invention:

Example 1 21-Chloro-9β,11β-epoxy-17α-hydroxy-16α-methyl-1,4-pregnadien-3,20-dione 9β,11β-Epoxy-17α,21-dihydroxy-16α-methyl-1,4-pregnadien-3,20-dione (50.0 g, about 98% pure) was charged into a 1 L three-neck flask, equipped with a thermometer, nitrogen inlet and mechanical stirrer. A nitrogen atmosphere was maintained throughout the reaction. 4-Toluenesulfonyl chloride (41.0 g, water content <0.3%) and $CH_2Cl_2$ (300 mL, water content <0.05%) were added, and the batch was cooled to –5° to 5° C. with stirring. Triethylamine (56.0 mL, water content <0.3 %) was slowly added to the batch (over a period of 2 to 3 hours) with effective stirring and careful control of the temperature between –5 and 5° C. The reaction temperature was maintained at –5° to 50° C. until the formation of 9β,11β-epoxy-17α,21-dihydroxy-16α-methyl-1,4-pregnadien-3,20-dione 21-tosylate was essentially complete (<0.4% 9β,11β-epoxy-17α,21-dihydroxy-16α-methyl-1,4-pregnadien-3,20-dione) as determined by HPLC (normally 3 to 4 hours). Then methanol (3.80 mL, water content <0.2%) was slowly added at –5° to 5° C., and the reaction mixture was allowed to warm to room temperature slowly over a period of 30 minutes.

The reaction mixture was then heated to 35° to 40° C. and this temperature was maintained until formation of 21-chloro-9β,11β-epoxy-17α-hydroxy-16α-methyl-1,4-pregnadien-3,20-dione was essentially complete as determined by HPLC (e.g., <0.1% of the 21-tosylate remaining, normally 4 to 8 hours). The reaction solution was then cooled to 0° to 5° C.

Example 2 21-Chloro-9β,11β-epoxy-17α-hydroxy-16α-methyl-1,4-pregnadien-3,20-dione 17-(2'-furoate)

Triethylamine (56.0 mL) was then added at 0° to 10° C. to the cold reaction solution from Example 1. Furoyl chloride (23.8 mL) was then added slowly at 0° to 10° C.; an exothermic reaction occurred, and the addition and temperature needed to be carefully controlled. The temperature of the reaction solution was maintained at 5° to 12° C. until <1.0% of 21-chloro-9β,11β-epoxy-17α-hydroxy-16α-methyl-1,4-pregnadien-3,20-dione remained as determined by HPLC (typically 10 to 14 hours). The reaction solution was then cooled to 0° to 5° C., and 2N HCl (about 170 mL) was slowly and carefully added with cooling and stirring. The reaction was exothermic, but the temperature was not allowed to exceed 20° C. The quantity of 2N HCl was adjusted so that the pH of the aqueous layer was between 1 and 2. The solution was transferred to a separatory funnel and allowed to settle for 15 minutes. The lower organic layer was then transferred back to a 1 L three-neck flask, and the aqueous layer was extracted with $CH_2Cl_2$ (100 mL). The organic layers (containing 21-chloro-9β,11 β-epoxy-17α-hydroxy-16α-methyl-1,4-pregnadien-3,20-dione 17-(2'-furoate)) were combined and cooled to –5° to 5° C.

Example 3 9α21-Dichloro-11β,17α-dihydroxy-16α-methyl-1,4-pregnadien-3,20-dione 17-(2'-furoate)

Concentrated HCl (160 mL, 36% or 12N) and then glacial acetic acid (50 mL) were added, and with each addition the temperature was maintained at –5° to +5° C. This temperature was further maintained until <5% 21-chloro-9β,11β-epoxy-17α-hydroxy-16α-methyl-1,4-pregnadien-3,20-dione 17-(2'-furoate) remained as monitored by HPLC (typically 1–3 hours). The reaction mixture was then warmed to 20° to 25° C., and this temperature was maintained until the amount of enol difuroate chlorohydrin (formed from the enol difuroate epoxide, which is mentioned in the section 'Background of the Invention') was less than 0.6% (typically 1 to 3 hours).

MeOH (50 mL) was added and the mixture was agitated until all solids dissolved. The lower organic layer was separated and the top aqueous layer was extracted with $CH_2Cl_2$ (25 mL), and the organic layers were combined. Further MeOH (50 mL) was added and the mixture was agitated until no solids remained. Water (200 mL) was then added to the organic layer and the pH was adjusted to 4–7 with 25% NaOH (about 18–25 mL). The organic solution (containing 9α,21-dichloro-11β,17α-dihydroxy-16α-methyl-1,4-pregnadien-3,20-dione 17-(2'-furoate)) was separated.

A 1 L three-neck flask was pre-calibrated at 300 ml, and the organic solution was added. The solution was concentrated by distillation to the precalibration mark (300 ml). Further MeOH (200 mL) was added, and the mixture was concentrated to 300 mL. (A precipitate may form at the end of this step.)

Further MeOH (200 mL) was again added, and the mixture was concentrated to 300 mL. The reaction mixture was slowly cooled to 20°–25° C. over 30 minutes and then cooled further to 5°–10° C., at which temperature it was agitated for about 1–2 hours. The 9α,21-dichloro-11β,17α-dihydroxy-16α-methyl-1,4-pregnadien-3,20-dione 17-(2'-furoate) was then filtered off and washed with cold methanol (0° to 10°C., 2×50 mL).

Example 4 Purification of 9α,21-dichloro-11β, 17α-dihydroxy-16α-methyl-1,4-pregnadien-3,20- dione 17-(2'-furoate)

The wet cake from Example 3 (9α,21-dichloro-11β,17α-dihydroxy-16α-methyl-1,4-pregnadien-3,20-dione 17-(2'-furoate)) was charged into a 1 L three-neck flask pre-marked at 300 mL. Decolorizing charcoal (5 g, 'Darco' ), $CH_3OH$ (200 mL) and $CH_2Cl_2$ (200 mL) were added, and the steroid was dissolved with stirring. The solution was then filtered, and the flask and filter paper were rinsed with $CH_2Cl_2$ (50 mL) and the rinsings were combined with the solution. The combined solution was then concentrated by distillation to 300 mL (sometimes yielding a slurry). MeOH (200 mL) was added and the mixture was concentrated to 300 mL. It was then cooled slowly to 20°–25° C. over 30 minutes and then cooled further to 5°–10° C., at which temperature it was agitated for about 1–2 hours. The 9α,21-dichloro-11β,17α-dihydroxy-16α-methyl-1,4-pregnadien-3,20-dione 17-(2'-furoate) was then filtered off and washed with cold methanol (0° to 10° C., 2×50 mL).

The 9α,21-dichloro-11β,17α-dihydroxy-16α-methyl-1,4-pregnadien-3,20-dione 17-(2'-furoate), was dried in a vacuum oven at 65°–70° C. until further loss on drying became less than 0.2%. 56 g of product were obtained (yield: 80%)

All publications and patent applications cited herein are incorporated by reference to the same extent as if each individual publication or patent application was specifically and individually indicated to be incorporated by reference.

While a number of embodiments of this invention are described herein, it is apparent that the embodiments can be altered to provide other embodiments that utilize the compositions and processes of this invention. Therefore, it will be appreciated that the scope of this invention includes alternative embodiments and variations which are defined in the foregoing Specification; and the invention is not to be limited to the specific embodiments that have been presented herein by way of example.

We claim:

1. A process for the preparation of a 17-ester of a 9α,21-dihalo-pregnane-11β,17α-diol-20-one, which comprises:
   (1) reacting a 9β,11β-epoxy-pregnane-17α,21-diol-20-one with an excess of an organic (aromatic or alkyl) sulfonyl halide, in the presence of a trialkylamine and an inert organic solvent to form the 21-sulfonate ester, and then adding to the reaction mixture an alcohol in an amount substantially equivalent to the excess of sulfonyl halide, to yield a 9β,11β-epoxy-21-halo-pregnane-17α-ol-20-one;
   (2) reacting the resulting 9β,11β-epoxy-21-halo-pregnane-17α-ol-20-one with an anhydride, chloride, or bromide of a carboxylic acid in the presence a trialkylamine, to form the 17-ester of the 9β,11β-epoxy-21-halo-pregnane-17α-ol-20-one; and then
   (3) reacting the resulting 9β,11β-epoxy-21-halo-pregnane-17α-ol-20-one 17-ester with aqueous hydrogen halide in the presence of an inert organic solvent to form the 17-ester of the 9α,21-dihalo-pregnane-11β, 17α-diol-20-one.

2. The process of claim 1 wherein:
   in step (1), the sulfonyl halide is an aromatic sulfonyl halide, which is used in about 0.01 to about 3 mol equivalents excess, the trialkylamine is a tri(lower alkyl)amine, the inert organic solvent is water-immiscible, and the alcohol is a lower primary alkanol;
   in step (2), the anhydride, chloride, or bromide of a carboxylic acid is the chloride of a heteroaryl carboxylic acid, and the trialkylamine is a tri(lower alkyl) amine; and
   in step (3), the aqueous hydrogen halide is aqueous HF, aqueous HCl, or aqueous HBr.

3. The process of claim 2 wherein the aqueous hydrogen halide is aqueous HCl, the inert organic solvent is water-immiscible, and the reaction is carried out in the presence of a water-miscible organic co-solvent.

4. A process for the preparation of a steroid of the formula II

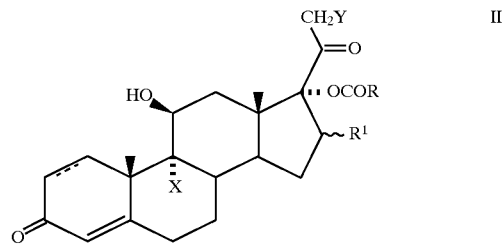

wherein:
   X is a fluorine, chlorine or bromine atom;
   Y is a fluorine, chlorine or bromine atom;
   RCO is a carboxylic acyl group;
   $R^1$ is hydrogen or a lower alkyl group (in the α- or β-configuration);
   and the broken line at the 1,2-positions indicates a single bond or a double bond;
which comprises:
   A) reacting a compound of the formula III

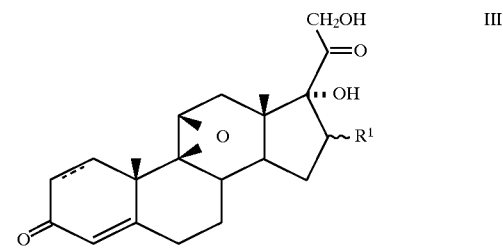

wherein $R^1$ and the dotted line are as defined above;
   with about 0.03 to about 3 mol equivalents excess of an organic (aromatic or alkyl) sulfonyl fluoride, chloride or bromide in the presence of a trialkylamine and an inert organic solvent to form the 21-sulfonate ester, and then adding to the reaction mixture a lower primary alkanol in an amount substantially equivalent to the excess of sulfonyl halide, to yield a compound of the formula IV:

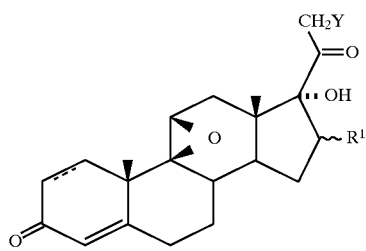

wherein R¹, Y and the dotted line are as defined above;

B) reacting the resulting compound of the formula IV with an anhydride, chloride, or bromide of a carboxylic acid RCOOH, wherein RCO is as defined above, in the presence of a trialkylamine, to form a compound of the formula:

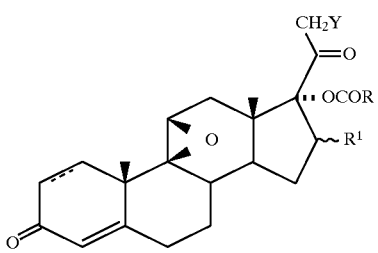

wherein RCO, R¹, Y and the dotted line are as defined above; and then

C) reacting the resulting compound of the formula V with aqueous HX, wherein X is as defined above, in the presence of an inert water-immiscible organic solvent to form a compound of the formula II defined above.

5. The process of claim 4 wherein X is F, Cl or Br, Y is Cl or Br, R¹ is an α-methyl group, the broken line at the 1,2-positions indicates a double bond, and RCO is a heterocyclic-carbonyl group.

6. The process of claim 5 wherein X is F or Cl, Y is Cl, and RCO is 2- or 3-furoyl, or 2- or 3-thenoyl.

7. The process of claim 6 wherein RCO is 2-furoyl.

8. The process of claim 4 wherein, in Step A, the aromatic sulfonyl halide is a chloride or bromide, the tri(lower alkyl)amine is dimethylethylamine, triethylamine, tripropylamine, tri(2-propyl)amine, or tributylamine, the inert organic solvent is methylene chloride, chloroform, carbon tetrachloride, diethyl ether, cyclohexane, or an aromatic hydrocarbon, and the aromatic sulfonyl halide is a benzenesulfonyl chloride which may be substituted with a chlorine atom or a methyl group.

9. The process of claim 4 wherein the tri(lower alkyl) amine is triethylamine, the inert organic solvent is methylene chloride, and the aromatic sulfonyl halide is 4-toluenesulfonyl chloride.

10. The process of claim 4 wherein the aromatic sulfonyl halide is used in an excess of about 0.3 to 1 equivalent, and the reaction is effected at a temperature of about −20° C. to room temperature.

11. The process of claim 4 wherein methanol is added to the reaction mixture, substantially equivalent to the excess of aromatic sulfonyl halide, and the 21-fluoro, chloro or bromo compound is allowed to form at 30°–40° C.

12. The process of claim 4 wherein the esterification is effected in the same reaction medium without isolation of the steroid product from Step A.

13. The process of claim 12 wherein the esterification is effected with from 1.5 to 2.0 mole of acid halide at 5°–15° C. for 5–15 hours.

14. The process of claim 4 wherein aqueous hydrogen halide (wherein the halide is fluoride, chloride or bromide) is then added to the solution of the steroid of the formula IV, together with an inert water-miscible organic solvent.

15. The process of claim 14 wherein the inert water-miscible organic solvent is glacial acetic acid.

16. The process of claim 4 wherein, in Step A, 9β,11β-epoxy-17α,21-dihydroxy-16α-methyl-1,4-pregnadien-3,20-dione is converted into its 21-tosylate by reaction with 1.1 to 2.5 equivalents of 4-toluenesulfonylchloride in triethylamine and methylene chloride at −10° to 10° C. for 1–10 hours.

17. The process of claim 16 wherein 9β,11β-epoxy-17α,21-dihydroxy-16α-methyl-1,4-pregnadien-3,20-dione 21-tosylate is then converted into 21-chloro-9β,11β-epoxy-17α-hydroxy-16α-methyl-1,4-pregnadien-3,20-dione by addition of methanol to the reaction mixture.

18. The process of claim 17 wherein, in Step B, 21-chloro-9β,11β-epoxy-17α-hydroxy-16α-methyl-1,4-pregnadien-3,20-dione from Step A is converted without isolation into 21-chloro-9β,11β-epoxy-17α-hydroxy-16α-methyl-1,4-pregnadien-3,20-dione 17-(2'-furoate) by reaction with 2-furoyl chloride in triethylamine and methylene chloride at 5°–15° C.

19. The process of claim 18 wherein, in Step C, triethylamine is first removed by extraction with mineral acid, and then 21-chloro-9β,11β-epoxy-17α-hydroxy-16α-methyl-1,4-pregnadien-3,20-dione 17-(2'-furoate) is converted into 9α,21-dichloro-11β,17α-dihydroxy-16α-methyl-1,4-pregnadien-3,20-dione 17-(2'-furoate) by reaction with about 12N aqueous HCl in acetic acid and methylene chloride, wherein the reaction is carried out at about 0° C. for 1–3 hours and then at about 20° C. for 2–4 hours.

20. The process of claim 19 wherein 21-chloro-9β,11β-epoxy-17α-hydroxy-16α-methyl-1,4-pregnadien-3,20-dione 17-(2'-furoate) is isolated by washing the reaction mixture to remove acids, and replacement of methylene chloride with methanol, whereby 21-chloro-9β,11β-epoxy-17α-hydroxy-16α-methyl-1,4-pregnadien-3,20-dione 17-(2'-furoate) precipitates.

21. The process of claim 4 for the preparation of 9α,21-dichloro-11β,17α-dihydroxy-16α-methyl-1,4-pregnadien-3,20-dione 17-(2'-furoate), which comprises:

A1) reacting 9β,11β-epoxy-17α,21-dihydroxy-16α-methyl-1,4-pregnadien-3,20-dione with 4-toluenesulfonyl chloride in the presence of triethylamine and methylene chloride to form the 21-tosylate, and then adding methanol whereby 21-chloro-9β,11β-epoxy-17α-hydroxy-16α-methyl-1,4-pregnadien-3,20-dione is formed;

B1) reacting 21-chloro-9β,11β-epoxy-17α-hydroxy-16α-methyl-1,4-pregnadien-3,20-dione (without isolation) with 2-furoyl chloride in the presence of triethylamine to yield 21-chloro-9β,11β-epoxy-17α-hydroxy-16α-methyl-1,4-pregnadien-3,20-dione 17-(2'-furoate), and then removing triethylamine and other water-soluble materials with an acid wash; and C1) reacting 21-chloro-9β,11β-epoxy-17α-hydroxy-16α-methyl-1,4-pregnadien-3,20-dione 17-(2'-furoate) (without isolation) with concentrated aqueous HCl in the presence of acetic acid to yield 9α,21-dichloro-11β,17α-dihydroxy-16α-methyl-1,4-pregnadien-3,20-dione 17-(2'-furoate).

22. The process of claim 21 wherein:

Step A1 is carried out with about 0.4 to 1.0 equivalents excess of 4-toluenesulfonylchloride in about 3–5 equivalents of triethylamine and sufficient methylene chloride at −5° to +5° C. for 2–4 hours; and then the excess of 4-toluenesulfonylchloride is removed by the addition of sufficient methanol, and the reaction mixture is heated at 35°–40° C. for 4–8 hours;

Step B1 is carried out at about 5°–15° C. and in the presence of 1.5 to 2 equivalents of 2-furoylchloride;

Step C1 is carried out with stirring at 0° C. for about 1–3 hours and then at about 20° C. for about 1–3 hours to yield 9α,21-dichloro-11β,17α-dihydroxy-16α-methyl-1,4-pregnadien-3,20-dione 17-(2'-furoate).

23. A process for the preparation of a steroid of the formula IIA

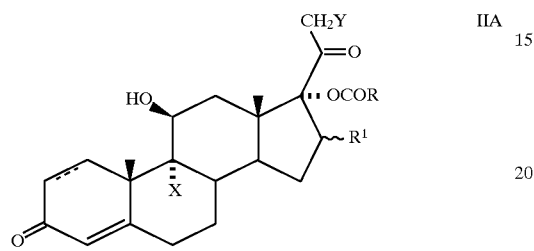

wherein:
X is a fluorine, chlorine or bromine atom;
Y is an iodine atom;
RCO is a carboxylic acyl group;
$R^1$ is hydrogen or an alkyl group (in the α- or β-configuration);
and the broken line at the 1,2-positions indicates a single bond or a double bond;
which comprises:
A) reacting a compound of the formula IIIA

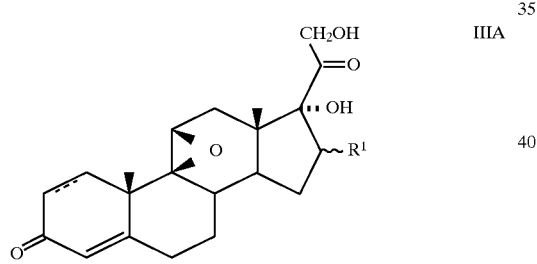

wherein $R^1$ and the dotted line are as defined above;

with about 0.03 to about 3 mol equivalents excess of an organic (aromatic or alkyl) sulfonyl chloride or bromide in the presence of a trialkylamine and an inert organic solvent to form the 21-sulfonate ester, and then adding to the reaction mixture an alkanol substantially equivalent to the excess of sulfonyl halide and at least one equivalent of an ionic iodide, to yield a compound of the formula IVA:

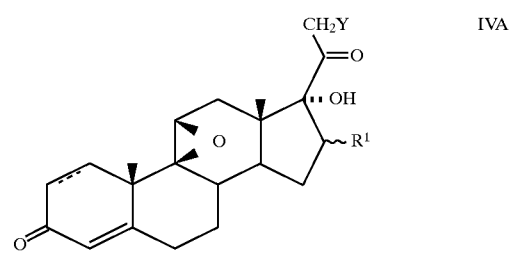

wherein $R^1$, Y and the dotted line are as defined above;

B) reacting the resulting compound of the formula IVA with an anhydride, chloride, or bromide of a carboxylic acid RCOOH, wherein RCO is as defined above, in the presence of a trialkylamine, to form a compound of the formula VA:

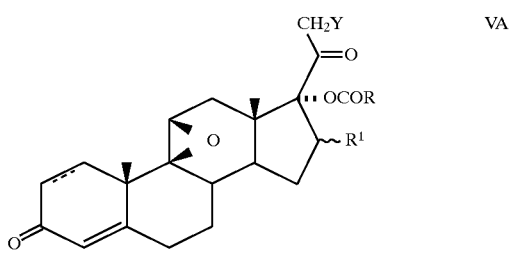

wherein RCO, $R^1$, Y and the dotted line are as defined above; and then

C) reacting the resulting compound of the formula VA with aqueous HX, wherein X is as defined above, in the presence of an inert organic solvent to form a compound of the formula II defined above.

* * * * *